United States Patent [19]
Lubowitz et al.

[11] Patent Number: 5,521,014
[45] Date of Patent: May 28, 1996

[54] EXTENDED MULTIDIMENSIONAL ETHER OR ESTER OLIGOMERS

[75] Inventors: Hyman R. Lubowitz, Rolling Hills Estates, Calif.; Clyde H. Sheppard, Bellevue, Wash.

[73] Assignee: The Boeing Company, Seattle, Wash.

[21] Appl. No.: 463,877

[22] Filed: Jun. 5, 1995

Related U.S. Application Data

[60] Division of Ser. No. 167,656, Mar. 14, 1988, which is a continuation-in-part of Ser. No. 810,817, Dec. 17, 1985, abandoned, which is a continuation-in-part of Ser. No. 726,258, Apr. 23, 1985, abandoned, which is a continuation-in-part of Ser. No. 519,394, Aug. 1, 1983, Pat. No. 5,120,787, Ser. No. 673,229, Nov. 20, 1984, Pat. No. 4,584,364, Ser. No. 536,350, Sep. 27, 1983, abandoned, Ser. No. 505,348, Jun. 17, 1983, Pat. No. 4,536,559, and Ser. No. 651,862, Sep. 18, 1984, abandoned, which is a continuation-in-part of Ser. No. 519,394, Ser. No. 673,229, Ser. No. 536,350, and Ser. No. 505,348, said Ser. No. 673,229, is a continuation of Ser. No. 576,790, Feb. 6, 1984, abandoned, which is a continuation-in-part of Ser. No. 321,119, Nov. 13, 1981, abandoned, said Ser. No. 536,350, is a continuation-in-part of Ser. No. 519,394, Aug. 1, 1983, abandoned.

[51] Int. Cl.[6] .................................... B32B 27/36
[52] U.S. Cl. .................. 428/482; 528/125; 528/126; 528/128; 528/171; 528/174; 528/192; 528/193; 528/210; 528/401; 528/503; 524/81; 428/480
[58] Field of Search .................... 528/125, 126, 528/128, 171, 174, 192, 193, 210, 401, 503; 524/81; 428/480, 482

[56] References Cited

U.S. PATENT DOCUMENTS

| | | | |
|---|---|---|---|
| 4,225,497 | 9/1980 | Baudouin et al. | 548/435 |
| 4,225,498 | 9/1980 | Baudouin et al. | 548/435 |
| 4,536,559 | 8/1985 | Lubowitz et al. | 528/170 |
| 4,579,957 | 4/1986 | Kanayama et al. | 548/521 |
| 4,617,390 | 10/1986 | Hoppe et al. | 544/197 |
| 4,661,604 | 4/1987 | Lubowitz et al. | 548/435 |
| 4,675,414 | 6/1987 | DeFusco et al. | 548/521 |
| 4,808,717 | 2/1989 | Saito et al. | 544/219 |
| 4,851,501 | 7/1989 | Lubowitz et al. | 528/170 |
| 5,210,213 | 5/1993 | Sheppard et al. | 548/435 |

FOREIGN PATENT DOCUMENTS 2722513  5/1977  Germany.

OTHER PUBLICATIONS

Worthy, Chem & Eng'g News (Feb. 22, 1988) pp. 19–21.

*Primary Examiner*—Samuel A. Acquah
*Attorney, Agent, or Firm*—John C. Hammar

[57] ABSTRACT

Crosslinkable, polyaromatic, polyether or polyester oligomers can have glass transition temperatures above 900° F. while exhibiting desirable toughness for aerospace applications and ease of processing. A plurality (i.e. three or more) of generally linear aryl arms extend outwardly like spokes from a central aromatic hub through ether or ester linkages. Each spoke usually includes electronegative linkages, and is capped with one or two crosslinking functionalities (i.e. unsaturated hydrocarbon sites) which may be thermally or chemically activated to complete the advanced composite during curing. Among other methods, linear and multidimensional polyether oligomers are synthesized using nitrophthalic anhydride or halophthalic anhydride, dialcohols, or polyols, diamines, and suitable end caps.

16 Claims, No Drawings

EXTENDED MULTIDIMENSIONAL ETHER OR ESTER OLIGOMERS

REFERENCE TO RELATED APPLICATIONS

The present application is a division of application Ser. No. 07/167,656 filed Mar. 14, 1988, which is a continuation-in-part application based upon U.S. patent application Ser. No. 06/810,817, filed Dec. 17, 1985, now abandoned, which was a continuation-in-part application based upon U.S. patent application Ser. No. 06/726,258, filed Apr. 23, 1985, now abandoned, which, in turn, is a continuation-in-part application based upon the following U.S. patent applications:

(a) Ser. No. 06/519,394, filed Aug. 1, 1983, now U.S. Pat. No. 5,120,787; and (b) Ser. No. 06/673,229, Nov. 20, 1984, now U.S. Pat. No. 4,584,364, which was a continuation of Ser. No. 06/576,790, filed Feb. 6, 1984, now abandoned, which was a continuation-in-part application based upon Ser. No. 06/321,119, filed Nov. 13, 1981, now abandoned; and (c) Ser. No. 06/536,350, filed Sep. 27, 1983, now abandoned, which was a continuation-in-part application based upon Ser. No. 06/519,394, filed Aug. 1, 1983, now abandoned; and (d) Ser. No. 06/505,348, filed Jun. 17, 1983, now U.S. Pat. No. 4,536,559; and (e) Ser. No. 06/651,862, filed Sep. 18, 1984, now abandoned, (in favor of continuation applications that ultimately resulted in U.S. Pat. No. 4,965,336) which was a continuation-in-part application based upon the applications that are listed in (a)–(d) above.

TECHNICAL FIELD

The present invention relates to polyether or polyester, crosslinkable, multidimensional oligomers that are useful in forming advanced composites, and, particularly, to oligomers that have high glass transition temperatures to produce thermally stable, solvent resistant, tough composites suitable for aerospace applications. The oligomers cure to composites at temperatures significantly below their potential use temperatures.

BACKGROUND OF THE INVENTION

Recently, chemists have sought to synthesize oligomers for high performance advanced composites suitable for aerospace applications. These composites should exhibit solvent resistance; be tough, impact resistant, and strong; be easy to process; and be thermoplastic. Oligomers and composites that have thermo-oxidative stability and, accordingly, can be used at elevated temperatures are particularly desirable.

While epoxy-based composites are suitable for many applications, their brittle nature and susceptibility to thermal or hydrolytic degradation make them inadequate for many aerospace applications, especially those applications which require thermally stable, tough composites. Accordingly, research has recently focused on polyimide composites to achieve an acceptable balance between thermal stability, solvent resistance, and toughness. Still the maximum temperatures for use of the polyimide composites, such as PMR-15, are about 600°–625° F., since they have glass transition temperatures of about 690° F. PMR-15 still suffers, however, from brittleness.

There has been a progression of polyimide sulfone compounds synthesized to provide unique properties or combinations of properties. For example, Kwiatkowski and Brode synthesized maleic-capped linear polyarylimides as disclosed in U.S. Pat. No. 3,839,287. Holub and Evans synthesized maleic- or nadic-capped, imido-substituted polyester compositions as disclosed in U.S. Pat. No. 3,729,446. We synthesized thermally stable polysulfone oligomers as disclosed in U.S. Pat. No. 4,476,184 or U.S. Pat. No. 4,536,559, and have continued to make advances with polyetherimidesulfones, polyheterocycles or heterocycle sulfones, polybutadienesulfones, and "star" or "star-burst" multidimensional oligomers. We have shown surprisingly high glass transition temperatures yet reasonable processing and desirable physical properties in many of these oligomers and their composites.

Polybenzoxazoles, such as those disclosed in our U.S. Pat. Nos. 4,965,336 and 4,868,270, may be used at temperatures up to about 750°–775° F., since these composites have glass transition temperatures of about 840° F. Some aerospace applications need composites which have even higher use temperatures while maintaining toughness, solvent resistance, ease of processing, formability, strength, and impact resistance.

Multidimensional oligomers, such as disclosed in our U.S. Pat. No. 5,210,213, are easier to process than some advanced composite oligomers since they can be handled at lower temperatures. Upon curing, however, the oligomers crosslink (homopolymerize) through their end caps so that the thermal resistance of the resulting composite is markedly increased with only a minor loss of stiffness, matrix stress transfer (impact resistance), toughness, elasticity, and other mechanical properties. Glass transition temperatures above 950° F. are achievable.

Commercial polyesters, when combined with well-known diluents, such as styrene, do not exhibit satisfactory thermal and oxidative resistance to be useful for aircraft or aerospace applications. Polyarylesters (i.e., arylates) are often unsatisfactory, also, since the resins often are semicrystalline which may makes them insoluble in laminating solvents, intractable in fusion, and subject to shrinking or warping during composite fabrication. Those polyarylesters that are soluble in conventional laminating solvents remain so in composite form, thereby limiting their usefulness in structural composites. The high concentration of ester groups contributes to resin strength and tenacity, but also makes the resin susceptible to the damaging effects of water absorption. High moisture absorption by commercial polyesters can lead to distortion of the composite when it is loaded at elevated temperature.

High performance, aerospace, polyester advanced composites, however, can be prepared using crosslinkable, end capped polyester imide ether sulfone oligomers that have an acceptable combination of solvent resistance, toughness, impact resistance, strength, processibility, formability, and thermal resistance. By including Schiff base (—CH=N—), imidazole, thiazole, or oxazole linkages in the oligomer chain, the linear, advanced composites formed with polyester oligomers of our copending application U.S. Ser. No. 726,259 can have semiconductive or conductive properties when appropriately doped.

Conductive and semiconductive plastics have been extensively studied (see, e.g., U.S. Pat. Nos. 4,375,427; 4,338,222; 3,966,987; 4,344,869; and 4,344,870), but these polymers do not possess the blend of properties which are essential for aerospace applications. That is, the conductive polymers do not possess the blend of (1) toughness, (2) stiffness, (3) elasticity, (4) ease of processing, (5) impact resistance (and other matrix stress transfer capabilities), (6) retention of properties over a broad range of temperatures, and (7) high temperature resistance that is desirable on aerospace advanced composites. The prior art composites are often too brittle.

Thermally stable multidimensional oligomers having semiconductive or conductive properties when doped with suitable dopants are also known and are described in our copending applications (including U.S. Ser. No. 773,381 to Lubowitz, Sheppard and Torre). The linear arms of the oligomers contain conductive linkages, such as Schiff base (—N=CH—) linkages, between aromatic groups. Sulfone and ether linkages are interspersed in the arms. Each arm is terminated with a mono- or difunctional end cap (i.e. an end cap having one or two crosslinking functionalities) to allow controlled crosslinking upon heat-induced or chemically-induced curing. Other "semiconductive" oligomers are described in our other copending applications.

Polyamide oligomers and blends are described in our U.S. Pat. Nos. 4,876,328; 4,935,523; and 4,847,333, and polyetherimide oligomers and blends are described in our U.S. Pat. No. 4,851,495.

Polyamideimides are generally injection-moldable, amorphous, engineering thermoplastics which absorb water (swell) when subjected to humid environments or immersed in water. Polyamideimides are generally described in the following patents: U.S. Pat. Nos. 3,658,938; 4,628,079; 4,599,383; 4,574,144; or 3,988,344. The thermal integrity and solvent-resistance can be greatly enhanced by capping amideimide backbones with monomers that present one or two crosslinking functionalities at each end of the oligomer, as described in our U.S. Pat. No. 5,104,967.

Interpenetrating or semi-interpenetrating networks are also known, such as those described by Egli et al. in "Semi-Interpenetrating Networks of LARC-TPI" available from NASA-Langley Research Center.

SUMMARY OF THE INVENTION

Glass transition temperatures above 900° F. are achievable with multidimensional oligomers which include crosslinking groups at the ends of linear aromatic ether or ester chains.

A plurality of chains radiate from a central cyclic hub (preferably an aromatic moiety) to provide an array that may be crosslinked into a multidimensional, thermally stable composite that has excellent toughness and that is easy to process prior to curing. The crosslinking groups (usually unsaturated hydrocarbons, such as nadic and acetylenic phenylimide moieties) also provide solvent resistance to the composites. Glass transition temperatures of about 950° F. are achievable, although the properties of the resulting oligomers may be tailored within broad ranges.

Preferred multidimensional oligomers have a central, aromatic hub and three, radiating, ether or ester chains, as shown in the general formula:

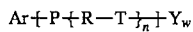

wherein

P=ether or ester;

w=3 or 4;

T=—O—, if P=—O—,

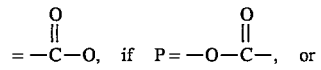

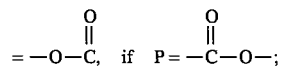

R=a linear hydrocarbon radical, generally including ether and electronegative ("sulfone") linkages selected from the group consisting of —SO$_2$—, —S—, —(CH$_3$)$_2$C—, —CO—, and —(CF$_3$)$_2$C—, and generally being a radical selected from the group consisting of:

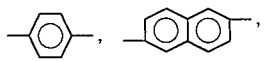

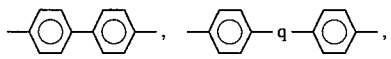

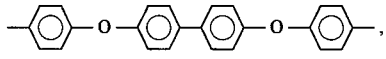

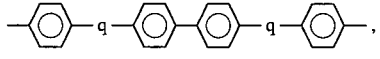

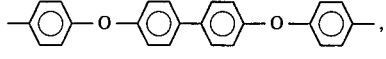

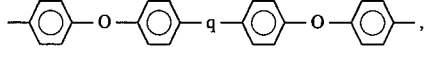

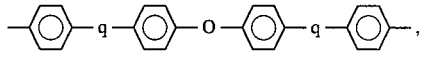

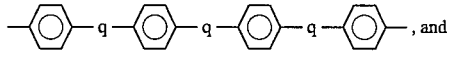

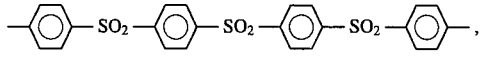

n=an integer such that the average molecular weight of —R—T— is up to about 3000 (and preferably 0 or 1);

q=—CO—, —SO$_2$—, —(CF$_3$)$_2$C—, —(CH$_3$)$_2$C—, or —S—;

Y=

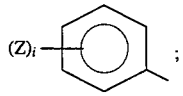

i=1 or 2;

Z=

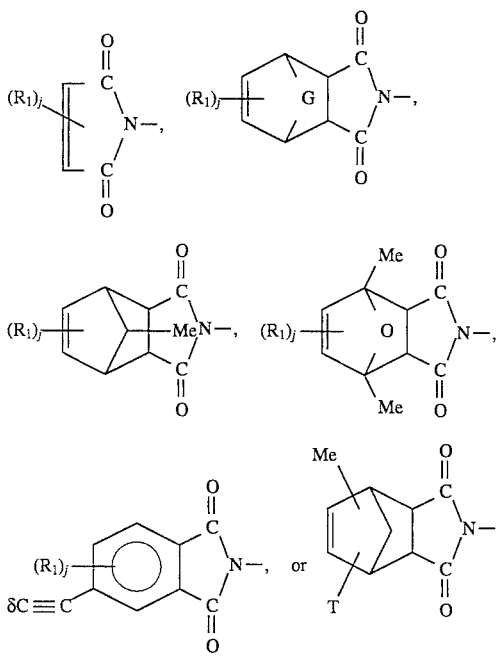

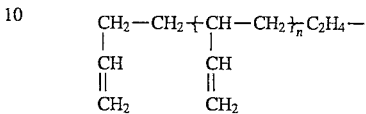

Me=methyl;
G=—CH$_2$—, —SO$_2$—, —S—, —O—, —SO—, —CO—, —CHR—, or —CR$_2$—
T=allyl or methallyl;
δ=hydrogen, lower alkyl, or phenyl;
j=0, 1 or 2; and
R$_1$=lower alkyl, aryl, substituted alkyl, substituted aryl, lower alkoxy, aryloxy, halogen, or mixtures thereof (the substituents including hydroxyl or halo- groups).

To produce the highest thermal stability Z preferably is either:

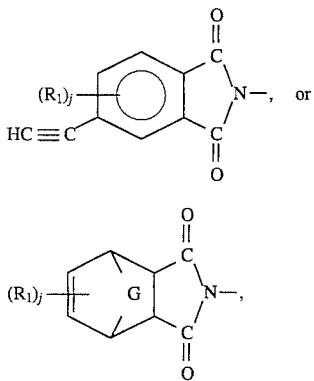

Multidimensional oligomers of this type are prepared by reacting substantially stoichiometric amounts of a multi-substituted hub, such as trihydroxybenzene (i.e., phloroglucinol), with chain-extending monomers and crosslinking end cap monomers. Suitable or preferred chain-extending monomers include dicarboxylic acid halides, dinitro compounds, diols (i.e., dihydric phenols, bisphenols, or dialcohols), or dihalogens. The hub is generally an aromatic compound, including a radical such as phenyl, biphenyl, naphthyl, azalinyl (i.e. melamine), or the like. The end cap monomers usually are phenols, acid halides, or nitro compounds.

Blends of the oligomers and compatible polymers are also contemplated, and may yield IPNs. The blends generally include the oligomer and an equimolar amount of a multi-dimensional polymer that has the same or substantially similar (i.e., analogous) structure but does not include crosslinking end caps. Synthesis of the polymer is quenched by using phenol, benzoic acid halide, nitrobenzene, or halobenzene instead of the end cap monomer.

Prepregs and composites are made from the oligomers or blends.

In some cases the end cap (Y) can be a butadiene radical of the general formula:

$$\begin{array}{ccc} CH_2-CH_2 + CH-CH_2 +_n C_2H_4- \\ | & | \\ CH & CH \\ \| & \| \\ CH_2 & CH_2 \end{array}$$

Oligomers using this end cap are generally prepared by reacting an acid halide hub with substantially a stoichiometric amount of a butadiene alcohol in a manner similar to the process described in our U.S. Pat. No. 4,547,553 for synthesizing linear polybutadiene oligomers. Chain extension using a polyol hub, dicarboxylic acid halides and diols can also be made.

Linear and multidimensional polyether-imide oligomers are also synthesized by condensing diols or polyols with nitrophthalic anhydride or halophthalic anhydride, diamines, and suitable end cap monomers.

Best Mode Contemplated for Making and Using the Present Invention

Thermally stable oligomers suitable for high temperature advanced composites are of particular interest in the present invention and are synthesized to include a high degree of aromatic groups. The stable aromatic bond energies produce an oligomer with outstanding thermal stability. Acceptable toughness and impact resistance is gained through selection of the linkages within the linear chains of aromatic groups radiating from the central aromatic hub. The linkages are ethers, esters, and electronegative ("sulfone") linkage selected from the group consisting of —CO—, —SO$_2$—, —S—, —(CF$_3$)$_2$C—, or —(CH$_3$)$_2$C—. Generally, —CO— and —SO$_2$— groups are preferred for cost, convenience, and performance. The group —S—S— should be avoided, since it is too thermally labile.

Although the preferred aromatic moieties are aryl groups, such as phenyl, biphenyl and naphthyl, other aromatic groups can be used, if desired, since the stablized aromatic bonds will also probably provide the desired thermal stability. For example, azaline (melamine) groups may be used. The aryl groups may include substituents, if desired, such as halogen, lower alkyl up to about 4 carbon atoms, lower alkoxy up to about 4 carbon atoms, or aryl. Substituents may create steric hindrance problems in synthesizing the oligomers or in crosslinking the oligomers into the final composites. These substituents may also effect the thermal stability of the resulting oligomers and composites. Unsubstituted phenyl groups are preferred for cost, convenience, and performance.

Improved performance and thermal stability is gained through the creation of a multidimensional, crosslinked oligomer, where a hub (generally an aromatic radical) includes a plurality of arms (chains, rays, or spokes) in the nature of a star to provide multidimensional, high density crosslinking through suitable terminal groups. Usually the hub will have three radiating arms to form a Y pattern. In some cases, four arms or more may be used. Including more arms leads to steric hindrance, however, as the hub may be too small. A trisubstituted phenyl or melamine hub is highly preferred with the arms being symmetrically placed about the hub.

The arms include crosslinking end groups (hydrocarbon insaturation), which improve the solvent-resistance of the composites, and which further stabilize the cured composite. These end groups may be thermally or chemically activated during the curing step to provide a strongly crosslinked, complex, multidimensional array of interconnected oligomers. Preferred end caps monomers include unsaturated hydrocarbon radicals selected from the group consisting of:

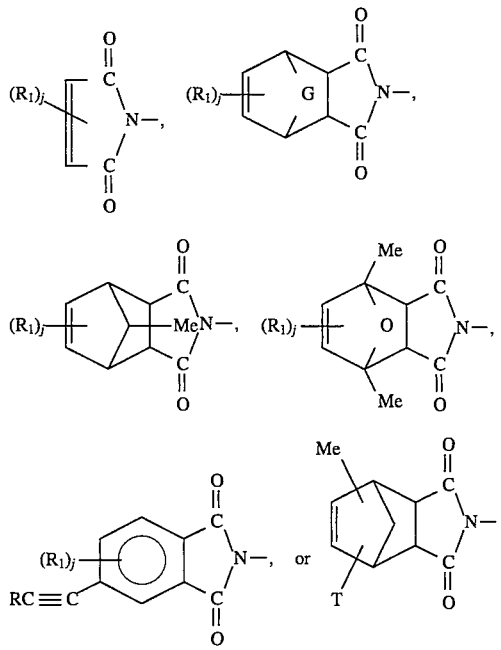

Me=methyl;
G=—$CH_2$—, —$SO_2$, —S—, —O—, —SO—, —CO—, —CHR—, or —$CR_2$—;
R=hydrogen, lower alkyl, or phenyl;
T=allyl or methallyl;
j=0, 1, or 2; and
$R_1$=lower alkyl, aryl, substituted alkyl, substituted aryl, lower alkoxy, aryloxy, halogen, or mixtures thereof (the substituents including hydroxyl or halo- groups).

When the goal is an advanced composite having a glass transition temperature above 900° F., and preferably above 950° F., the crosslinking end caps should have high thermal stability and high thermal activation temperatures. The end cap monomers in this case should include radicals selected from the group:

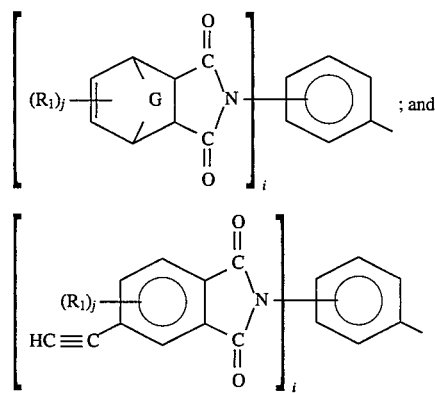

wherein i=1 or 2 (and, preferably, 2) and $R_1$, j, and G are as previously defined. Preferably j=0 and G=—$CH_2$— or —O—. The highest thermal stabilities are probably achievable when G=—$CH_2$— and $R_1$=phenyl or methyl, or, in the acetylene case, when j=0.

In some circumstances (especially where high thermo-oxidative stability is not as significant a concern), the end cap monomer can include a butadiene radical of the general formula:

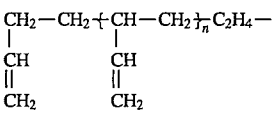

Ethynyl, trimethylsilylethynyl, and phenylethynyl end caps may also be used, if desired. These end caps will probably allow curing at lower temperatures, and will probably produced composites of lower thermal stability.

The preferred oligomers of the present invention, accordingly, are polyethers or polyesters having the general formula:

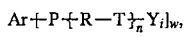

wherein Ar=aromatic moiety, preferably phenyl or azaline;

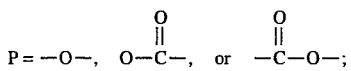

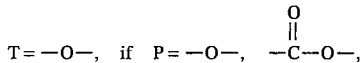

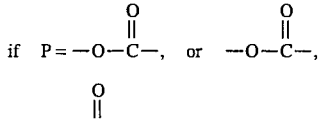

R=a aromatic chain, usually having ether and/or electronegative "sulfone" linkages; for example,

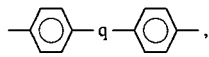

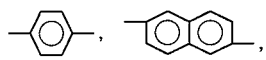

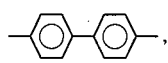

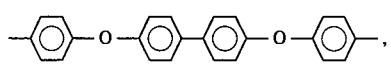

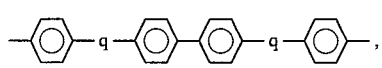

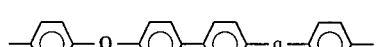

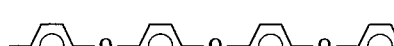

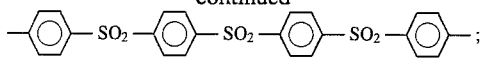

w=a small integer greater than or equal to 3 (and usually 3 or 4);

n=an integer such that the average molecular weight of —R—T— is up to about 3000 (and is preferably 0 or 1);

q=an electronegative group, preferably —CO—, —S—, —(CF$_3$)$_2$C—, or —SO$_2$—, and most preferably —CO— or —SO$_2$—; and Y=a crosslinkable end cap radical as previously described End caps with two crosslinking functionalities (i.e., i=2) are expected to yield the highest crosslinked arrays, since the density of crosslinking functionalities is the highest.

A trisubstituted phenyl hub is highly preferred with the chains being symmetrically placed about the hub. Biphenyl, naphthyl, or azaline (e.g., melamine) may also be used as the hub radical along with other aromatic moieties, if desired. Cyuranic acid halide is a particularly preferred starting material because of availability, cost, and convenience.

Triazine derivatives can be used as the hub. These derivatives are described in U.S. Pat. No. 4,574,154 and have the general formula:

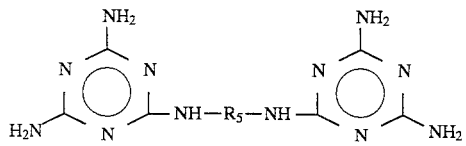

wherein R$_5$ is a divalent hydrocarbon residue containing 1–12 carbon atoms (and, preferably, ethylene) by reacting the amine functionalities with phthalic acid anhydride to form arms that include imide linkages and terminal acid functionalities (that can be converted to acid halides, if desired). The triazine derivatives of U.S. Pat. No. 4,617,390 (or the acid halides) can also be used as the hub.

Hubs suitable for making multidimensional oligomers of the present invention can also be made by reacting polyol aromatic hubs, such as phloroglucinol, with nitrobenzoic acid or nitrophthalic acid to form ether linkages and active, terminal carboxylic acid functionalities. The nitrobenzoic acid products would have three active sites while the nitrophthalic acid products would have six; each having the respective formula:

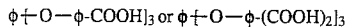

wherein φ=phenyl. Of course other nitro/acids can be used.

The polyol hub may be a compound such as those described in U.S. Pat. No. 4,709,008 to tris(hydroxyphenyl)alkanes of the general formula:

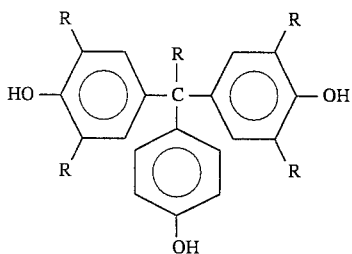

wherein R=hydrogen or methyl and can be the same or different. The polyols are made by reacting, for example, 4-hydroxybenzaldehyde or 4-hydroxyacetophenone with an excess of phenol under acid conditions (as disclosed in U.S. Pat. Nos. 4,709,008; 3,579,542; and 4,394,469).

Hubs can also be formed by reacting the corresponding halo-hub (such a tribromobenzene) with aminophenol to form triamine compounds represented by the formula:

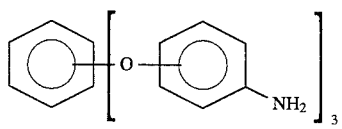

which can then be reacted with an acid anhydride to form a polycarboxylic acid of the formula:

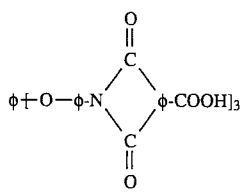

wherein φ=phenyl; the hub being characterized by an intermediate ether and imide linkage connecting aromatic groups. Thio-analogs are also contemplated, in accordance with U.S. Pat. No. 3,933,862.

Phenoxyphenyl sulfone arms radiating from a hub with either an active, terminal amine or carboxylic acid are also precursors for making suitable hubs and subsequently multidimensional oligomers of the present invention, especially those having butadiene end caps.

The best results and greatest ease of processing are likely to occur when the lengths of the arms are minimized. The highest thermal stabilities are believed to be achievable with arms that include a small number of unsubstituted phenyl groups and that are capped with crosslinking monomers that have two crosslinking functionalities. The end cap monomers may be condensed directly with the hubs.

The oligomers can be prepared by condensing simultaneously substantially stoichiometric amounts of the polyol hub such as phloroglucinol, Y—OH, and, for example, a dicarboxylic acid halide selected from the group consisting of:

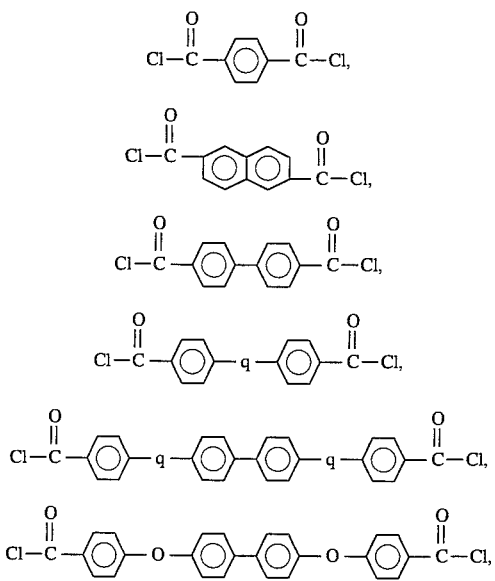

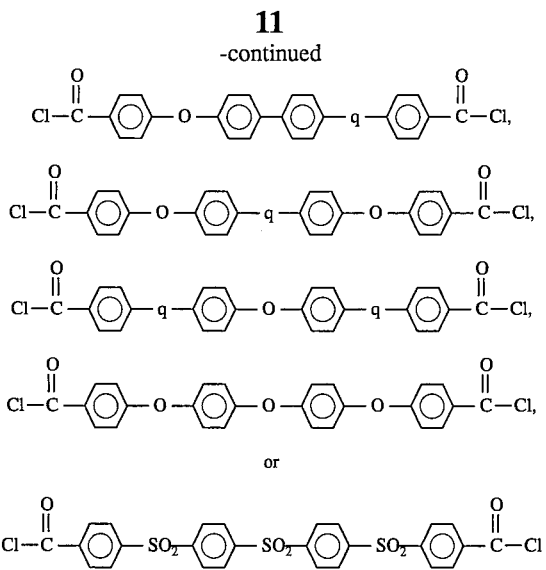

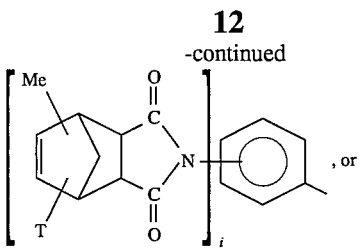

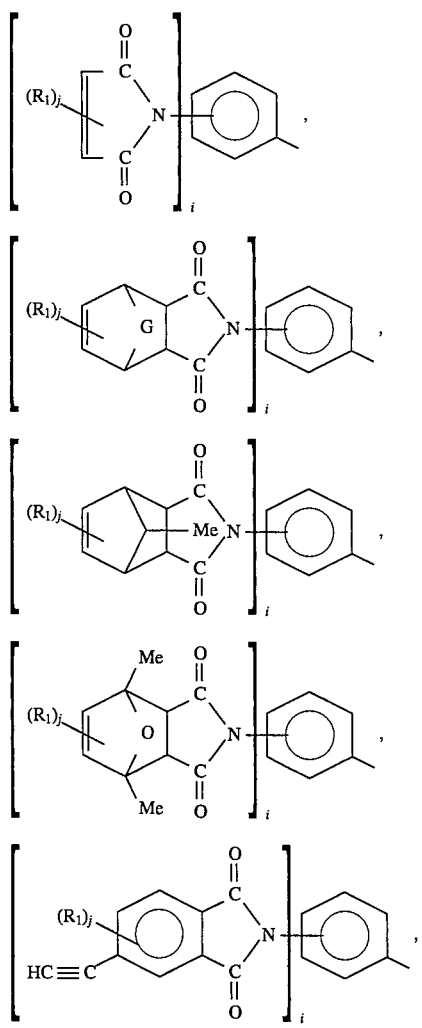

under an inert atmosphere (N$_2$ purge) to produce the star (i=1) or star-burst (i=2) oligomers. As previously described, Y= and preferably:

wherein i=1 or 2; R$_1$=lower alkyl, lower alkoxy, aryl, substituted alkyl, substituted aryl, aryloxy, or mixtures thereof; j=0, 1, or 2; G=—CH$_2$—, —O—, —S—, —SO$_2$—, —SO—, —CO—, CHR—, or —CR$_2$— (preferably —CH$_2$—); n=a small integer; Me=methyl; T=allyl or methallyl,; and R=hydrogen, lower alkyl, or phenol.

Generally the ratio of reactants is about 1 mole of the aromatic hub to at least 3 moles of end cap compounds to at least 3 moles of polyaryl chains. The arms usually include phenoxyphenyl sulfone, phenoxyphenyl ether, or phenyl sulfone moieties to supply the desired impact resistance and toughness to the resulting advanced composite (through "sulfone" swivels) without loss of the desired thermal stability.

The oligomers are easy to process and handle. They are suitable for forming prepregs by lay up in conventional solvents or carriers on suitable fabrics by conventional prepreg techniques. Rigid composites are made from the oligomers or prepregs by curing the oligomers at an elevated temperature in a conventional vacuum bag curing operation.

The oligomers include ether (—O—) or ester

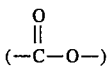

linkages, which are suitable for the intended uses of the advanced composites, and add to the thermal stability, impact resistance, and toughness.

A second synthetic mechanism for making the oligomers involves the reaction of a halogenated or polynitro aromatic hub with suitable amounts of dialcohols and a carboxylic acid chloride terminated end cap group. Again, the reactants are mixed together and are generally reacted at elevated temperatures under an inert atmosphere. Generally for either mechanism, the reactants are dissolved in a suitable solvent such as benzene, toluene, xylene, DMAC or mixtures and are refluxed to promote the reaction. Triethylamine can be added to catalyze the reaction.

The preferred aromatic hub in this circumstance is

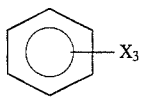

wherein X=halogen (normally chlorine). Cyuranic acid halide is also a preferred hub, if polyesters are being prepared.

The end cap groups used in this alternate mechanism are preferably selected from the group consisting of

wherein

X=halogen, usually chlorine, and

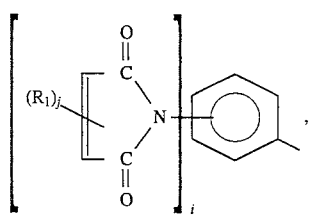

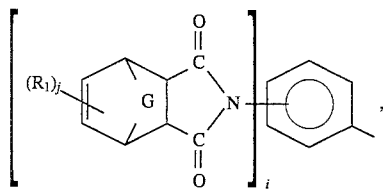

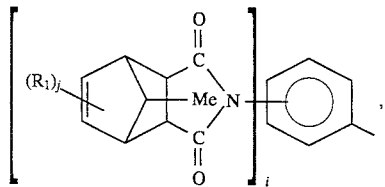

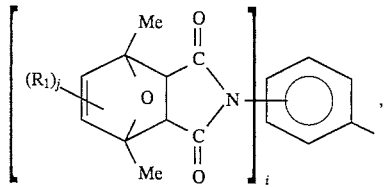

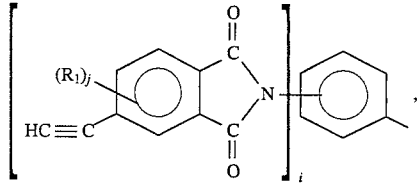

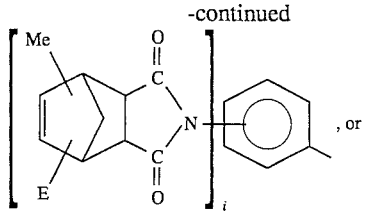

$$\begin{array}{ccc} CH_2-CH_2+CH-CH_2\overline{\jmath_n}\,C_2H_4- \\ | & | \\ CH & CH \\ \| & \| \\ CH_2 & CH_2 \end{array}$$

Suitable oligomers can also be made by directly reacting polyol hubs (such as phloroglucinol) or halogenated aromatic hubs with end cap groups having the corresponding halide, acid halide, nitro or alcohol (phenol) reactive functionality. For example,

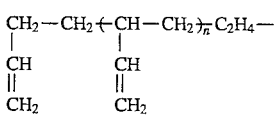

can be mixed with

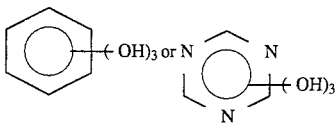

or Y - X, wherein Y and X are as previously defined, to form oligomers without chain extenders. These oligomers possess the desired blend of properties resulting in high thermal stability, toughness, impact resistance, and processability.

Similarly,

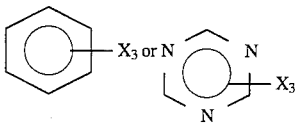

can be reacted with Y - OH to form suitable oligomers. Preliminary experiments show that glass transition temperatures as high as 975° F. are achievable with oligomers of this general type.

Suitable dicarboxylic acid halides (or its polybasic acid equivalent, if desired) include an aromatic chain segment selected from the group consisting of:

(a) phenyl; (b) naphthyl; (c) biphenyl;

(d) a polyaryl electronegative "sulfone" divalent radical of the general formula:

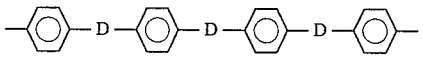

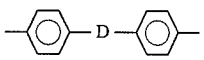

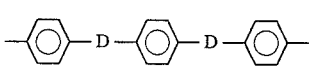

wherein $D=-S-$, $-O-$, $-CO-$, $-SO_2-$, $-(CH_3)_2C-$, $-(CF_3)_2C-$, or mixtures thereof throughout the chain; or (e) a divalent radical having conductive linkages, illustrated by Schiff base compounds selected from the group consisting of:

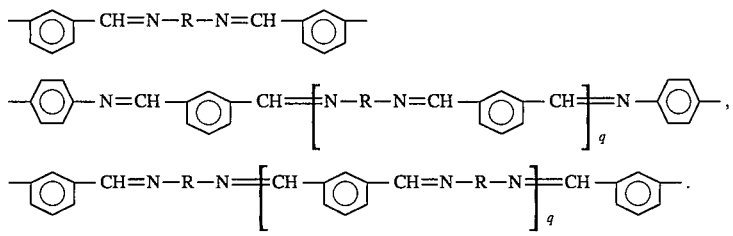

wherein R is selected from the group consisting of:

phenyl; biphenyl; naphthyl; or a divalent radical of the general formula:

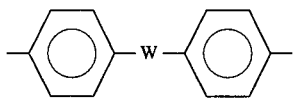

wherein W=—SO$_2$— or —CH$_2$—; and q=0-4; or

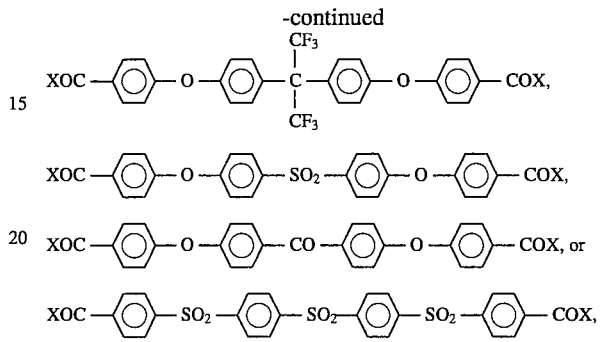

Schiff base dicarboxylic acids and diacid halides can be prepared by the condensation of aldehydes and aminobenzoic acid (or other amine acids) in the general reaction scheme:

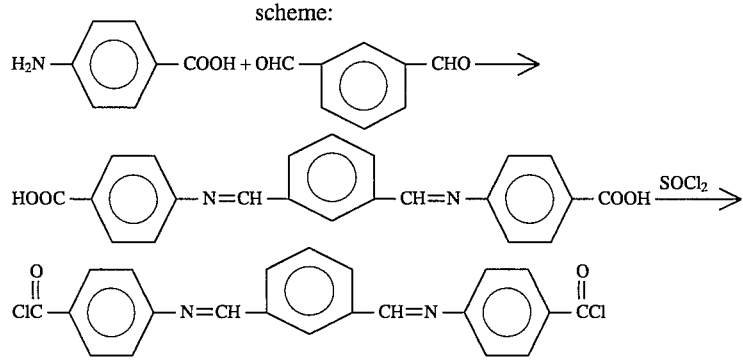

or similar syntheses.

Other diacid halides that can be used, but that are not preferred, are disclosed in U.S. Pat. No. 4,504,632, and include:

adipylchloride,
malonyl chloride,
succinyl chloride,
glutaryl chloride,
pimelic acid dichloride,
suberic acid dichloride,
azelaic acid dichloride,
sebacic acid dichloride,
dodecandioic acid dichloride,
phthaloyl chloride,
isophthaloyl chloride,
terephthaloyl chloride,
1,4-naphthalene dicarboxylic acid dichloride, and
4,4'-diphenylether dicarboxylic acid dichloride.

Polyaryl or aryl dicarboxylic acid halides (i.e. diacid halides) are preferred to achieve the highest thermal stabilities in the resulting oligomers and-composites insofar as aliphatic bonds are not as thermally stable as aromatic (f) a divalent radical of the general formula:

wherein R$^1$=a C$_2$ to C$_{12}$ divalent aliphatic alicyclic, or aromatic radical, and, preferably, phenyl (as described in U.S. Pat. No. 4,556,697).

Thiazole, oxazole, or imidazole linkages, especially between aryl groups, may also be used as the conductive linkages to form the conductive or semiconductive oligomers.

The preferred dicarboxylic halides include:

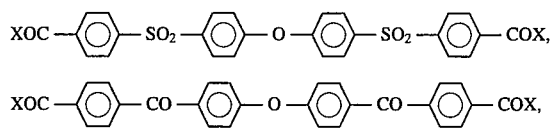

bonds. Particularly preferred compounds include intermediate electronegative (i.e., "sulfone") linkages to improve toughness of the resulting oligomers.

Diacid halides prepared by reacting an acid anhydride of the general formula:

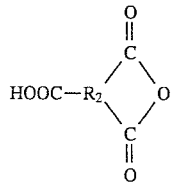

with a diamine may also be used, wherein $R_2$ is a trivalent hydrocarbon radical, and, generally, phenyl.

The dialcohol (i.e. diol, dihydric phenol, or bisphenol) is generally selected from the group consisting of:

HO - Ar - OH;

HO - Ar - L - Ar'- L - Ar - OH;

HO - Ar'- L - Ar - L - Ar'- OH;

wherein L=—CH$_2$—, —(CH$_3$)$_2$C—, —(CF$_3$)$_2$C—, —O—, —S—, —SO$_2$—, or —CO—;

Ar'=

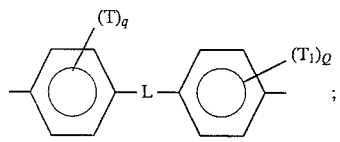

Ar=

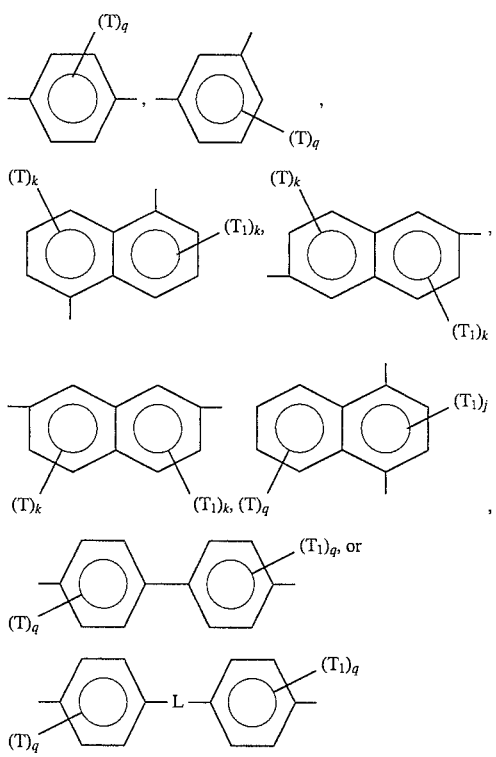

T and $T_1$=lower alkyl, lower alkoxy, aryl, aryloxy, substituted alkyl, substituted aryl, halogen, or mixtures thereof;
q=0–4;
k=0–3; and
j=0, 1, or 2, The dialcohols also include hydroquinone; bisphenol-A; p,p'-biphenol; 4,4'-dihydroxydiphenylsulfide; 4,4'-dihydroxydiphenylether; 4,4'-dihydroxydiphenylisopropane; 4,4'-dihydroxydiphenylhexafluoropropane; a dialcohol having a Schiff base segment, the radical being selected from the group consisting of:

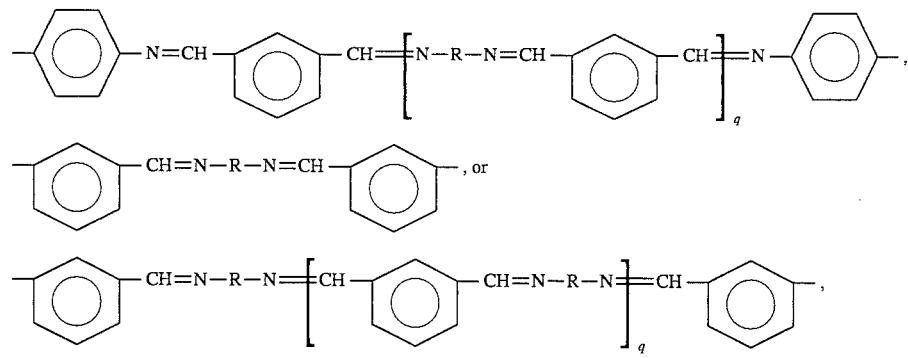

wherein R is selected from the group consisting of:
phenyl;
biphenyl;
naphthyl; or a radical of the general formula:

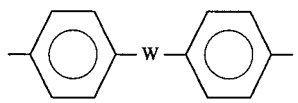

wherein W=—CH$_2$— or —SO$_2$—; or a dialcohol selected from the group:

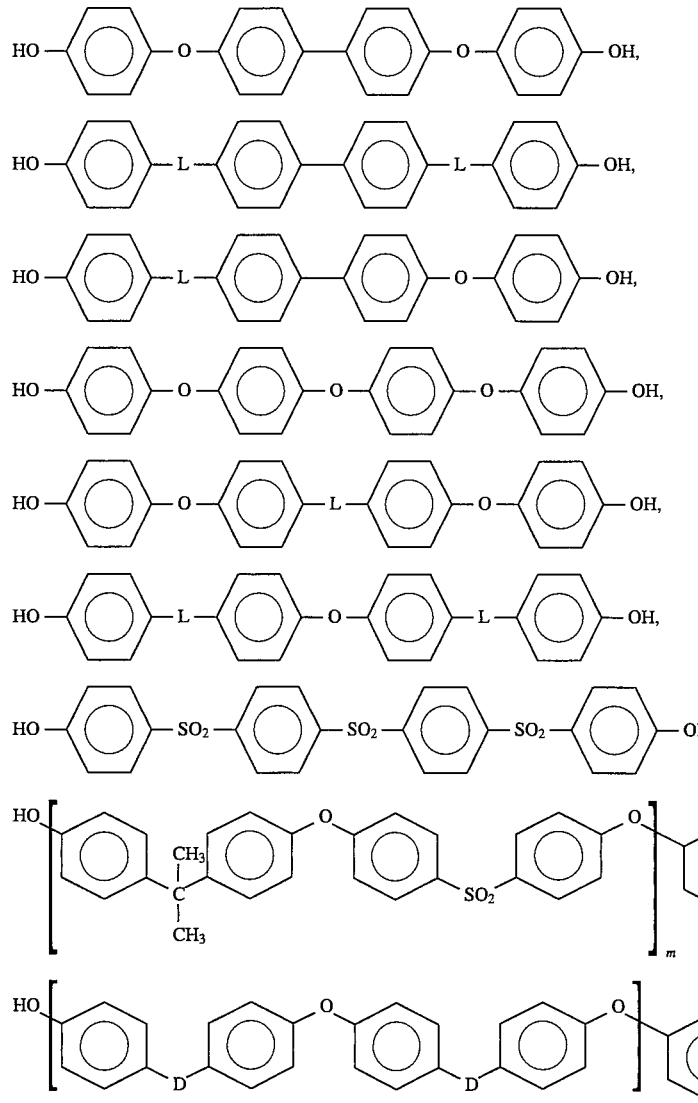

wherein L is as defined above;
Me=methyl;
m=an integer, generally less than 5, and preferably 0 or 1; and
D=any of —CO—, —SO$_2$—, or —(CF$_3$)$_2$C—.

While bisphenol-A is preferred in the etherimide synthesis (because of cost and availability), the other dialcohols can be used to add rigidity to the oligomer without significantly increasing the average formula weight, and, therefore, can increase the solvent resistance. Random or block copolymers are possible.

Furthermore, the dialcohols may also be selected from the those described in U.S. Pat. Nos. 4,584,364; 3,262,914; or 4,611,048.

Dialcohols of this nature are commercially available. Some may be easily synthesized by reacting halide intermediates with bis-phenates, such as by the reaction of 4,4'-dichlorodiphenylsulfone with bis(disodium biphenolate).

Schiff base diols are prepared by the condensation of aldehydes and amines under the general reaction schemes:

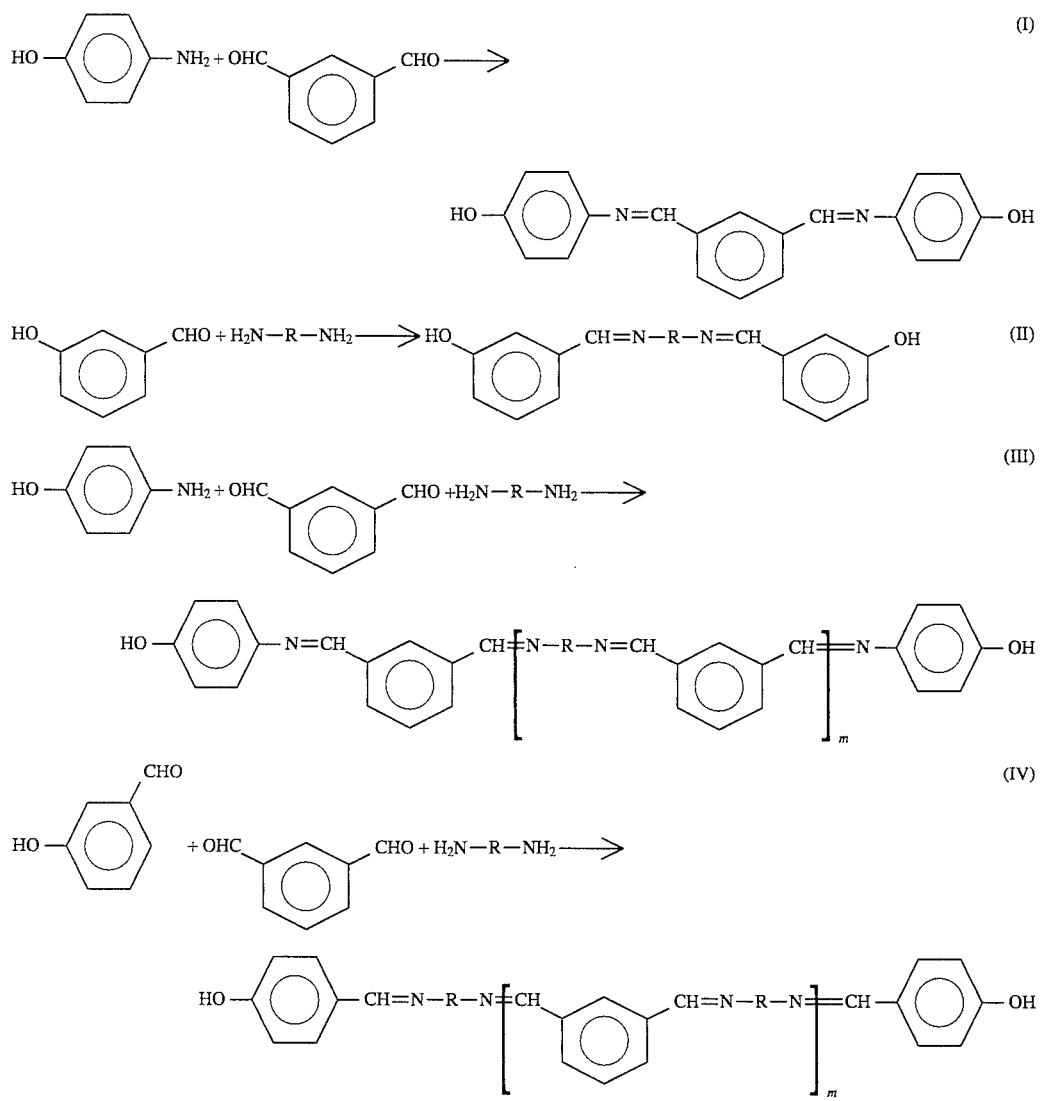

Polyester Schiff base compounds are then prepared by condensing the Schiff base diols with end cap acid halides (or carboxylic acids) and diacid halide chains.

Schiff base acid halides can be prepared by the general reaction scheme:

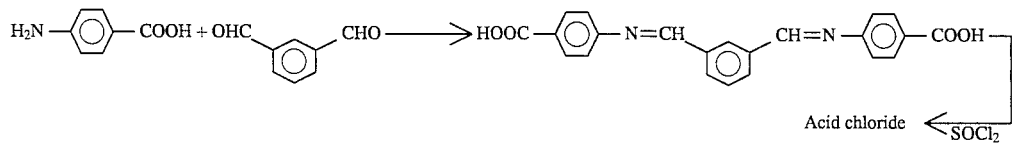

or similar schemes as with the diols. The resulting polyesters are made by condensing the acid halides with suitable diols.

While illustrated for preparing Schiff base diacid halides and diols, these reaction schemes are representative of the processes used to prepare any of the diacid halides or diols used in the polymerization reactions. Inexpensive, commercially available starting compounds are used.

Of course, as indicated previously an ether linkage can also be formed by the reaction of a hydroxyl with a nitro functionality. For example, phloroglucinol may be reacted with a dinitro compound and an imidophenol end cap monomer to form multidimensional ether oligomers. Alternatively a nitro hub can be reacted with a dialcohol and a nitro end cap or halo-end cap.

Suitable dinitro compounds for this alternative synthesis can be prepared, for example, by reacting nitrophthalic anhydride (as described in U.S. Pat. Nos. 4,297,474 and 3,847,869) with a diamine. In this case, suitable diamines include:

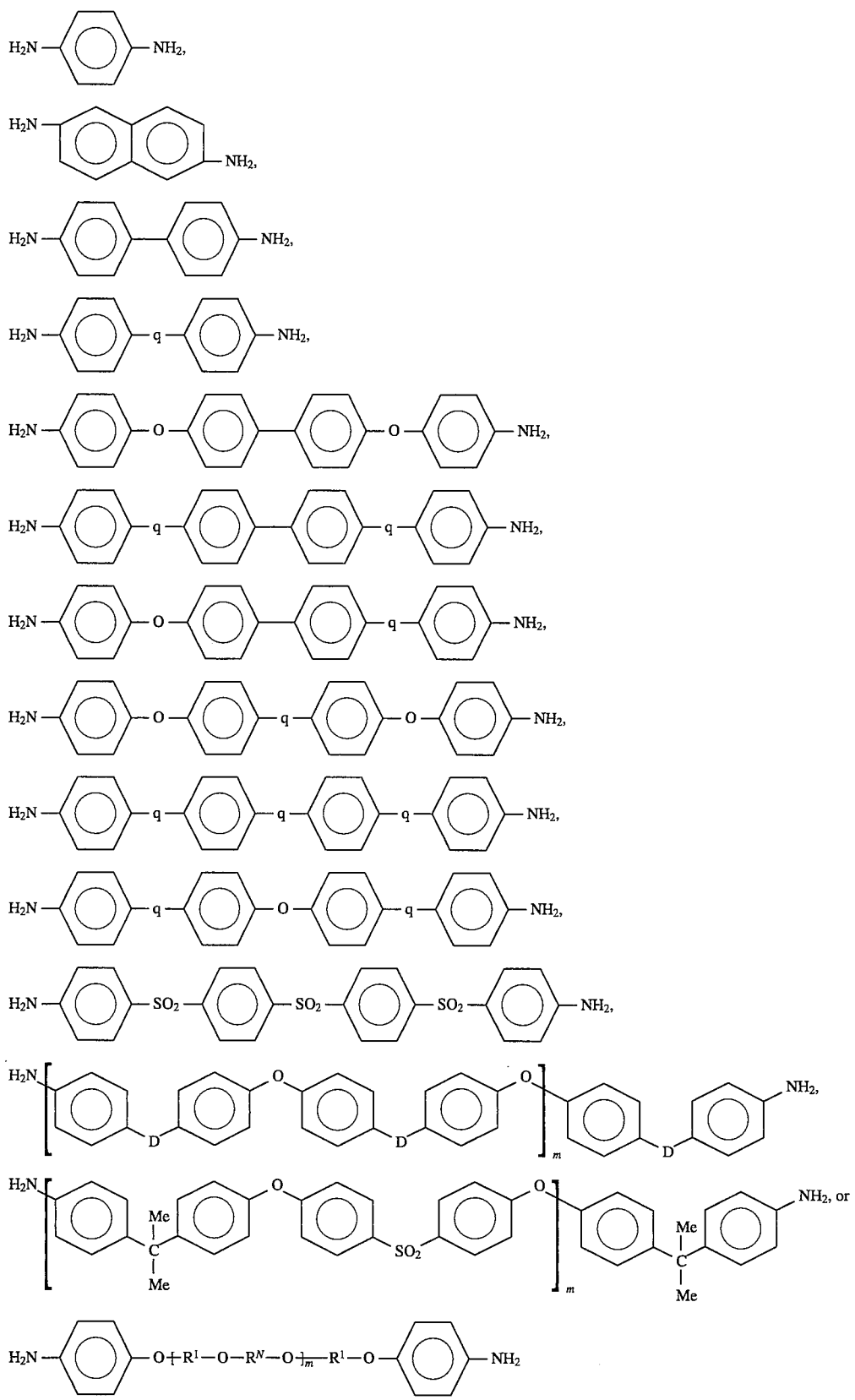

wherein $R^1=$

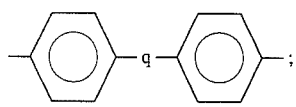

$R''=$

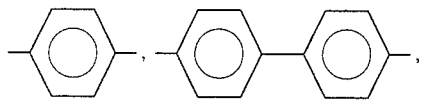

and R'' is

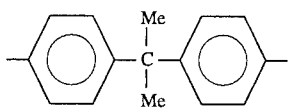

so that the phenoxyphenyl sulfone diamines include:

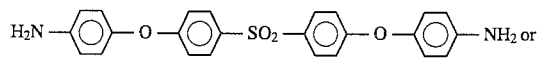

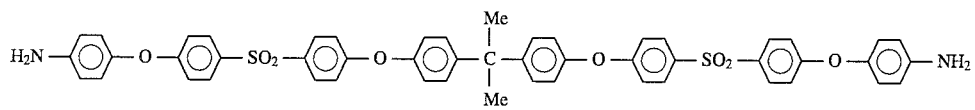

-continued

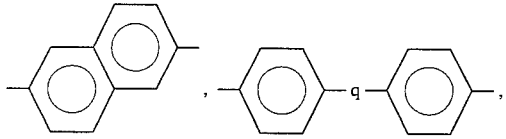

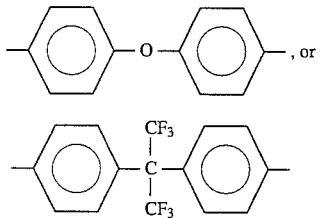

$q=$—$SO_2$—, —CO—, —S—, or —$(CF_3)_2$C—, and preferably —$SO_2$— or —CO—;
Me=methyl;
m=an integer, generally less than 5, and preferably 0, 1, or 2;
D=any of —CO—, —$SO_2$—, or —$(CF_3)_2$C—; and
X=halogen.

Diamines comparable to the diacid halides previously described and including "Schiff base" conductive linkages (particularly —N═CH—) are also contemplated as suitable diamines.

Other diamines that may be use, but that are not preferred, include those described in U.S. Pat. Nos. 4,504,632; 4,058,505; 4,576,857; 4,251,417; and 4,215,418. The aryl or polyaryl "sulfone" diamines previously described are preferred, since these diamines are soluble in conventional synthetic solvents and provide high thermal stability to the resulting oligomers and composites.

Particularly preferred ethersulfone (i.e. phenoxyphenyl sulfone) diamines are those in which $R_1$ is

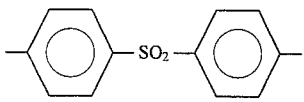

The molecular weights of these diamines can be easily varied from approximately 500 to about 2000. Using lower molecular weight diamines enhances the mechanical properties of the difunctional polyimide oligomers, each of which has alternating ether "sulfone" segments in the backbone.

Phenoxyphenyl sulfone diamines of this general nature can be prepared by reacting two moles of aminophenol with (n+1) moles of an aryl radical having terminal, reactive halide functional groups (dihalogens), such as 4,4'-dichlorodiphenyl sulfone, and a suitable bisphenol (i.e., dihydric phenol or diol). The bisphenol is preferably selected from the group consisting of:

2,2-bis-(4-hydroxyphenyl)-propane (i.e., bisphenol-A);
bis-(2-hydroxyphenyl)-methane;
bis-(4-hydroxyphenyl)-methane;
1,1-bis-(4-hydroxyphenyl)-ethane;
1,2-bis-(4-hydroxyphenyl)-ethane;
1,1-bis-(3-chloro-4-hydroxyphenyl)-ethane;
1,1-bis-(3,5-dimethyl-4-hydroxyphenyl)-ethane;
2,2-bis-(3-phenyl-4-hydroxyphenyl)-propane;
2,2-bis-(4-hydroxynaphthyl)-propane
2,2-bis-(4-hydroxyphenyl)-pentane;
2,2-bis-(4-hydroxyphenyl)-hexane;
bis-(4-hydroxyphenyl)-phenylmethane;
bis-(4-hydroxyphenyl)-cyclohexylmethane;
1,2-bis-(4-hydroxyphenyl)-1,2-bis-(phenyl)-ethane;
2,2-bis-(4-hydroxyphenyl)-1-phenylpropane;
bis-(3-nitro-4-hydrophenyl)-methane;
bis-(4-hydroxy-2,6-dimethyl-3-methoxyphenyl)-methane;
2,2-bis-(3,5-dichloro-4-hydroxyphenyl)-propane;
2,2-bis-(3-bromo-4-hydroxyphenyl)-propane;
or mixtures thereof, as disclosed in U.S. Pat. No. 3,262,914. Bisphenols having aromatic character (i.e., absence of aliphatic segements), such as bisphenol A, are preferred.

The dihalogens in this circumstance preferably are selected from the group consisting of:

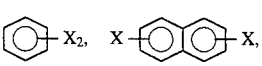

-continued

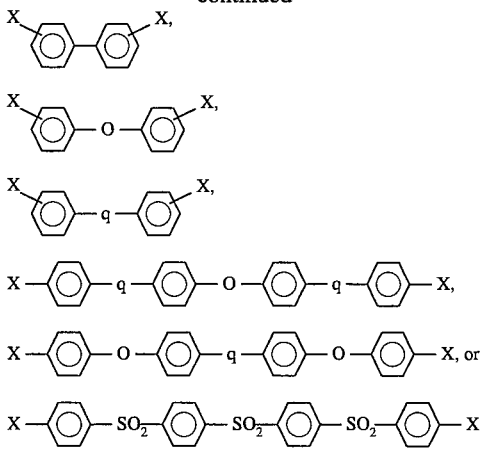

wherein X=halogen, preferably chlorine; and
q=—S—, —SO₂—, —CO—, —(CH₃)₂C—, and —(CF₃)₂C—, and preferably either —SO₂— or —CO—.

The condensation reaction creates ether diamines that ordinarily include intermediate "sulfone" linkages. The condensation generally occurs through a phenate mechanism in the presence of K₂CO₃ or another base in a DMSO/toluene solvent. Additional methods for preparing phenoxyphenysulfones of this general type are disclosed in U.S. Pat. Nos. 3,839,287 and 3,988,374.

In any of the syntheses, the dialcohol can be replaced by a comparable disulfhydryl of the formula: HS-R₂-SH. Mixtures of dialcohols, or disulfhydryls, or dialcohols and disulfhydryls can be used.

The oligomers may also be formed by the attachment of chains to the hub followed by chain termination in two steps. For example, tribromobenzene may be mixed with p-aminophenol and 4,4'-dibromodiphenylsulfone and reacted under an inert atmosphere at an elevated temperature to achieve an amino terminated "star" of the general formula:

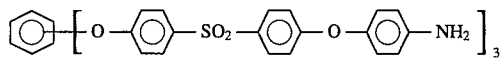

which can be reacted with an end cap anhydride, such as one selected from the group consisting of:

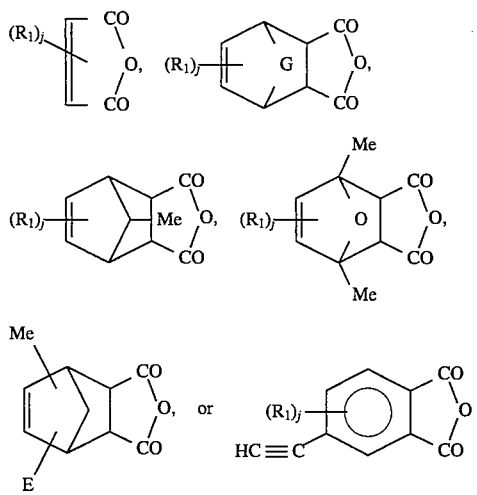

wherein, as previously defined, Me=methyl;
G=—O—, —SO₂—, —CH₂—, —S—, —SO—, —CO—, —CHR—, or —CR₂—;
E=allyl or methallyl;
R=hydrogen, lower alkyl, or phenyl;
R₁=lower alkoxy, aryl, substituted aryl, lower alkyl, substituted alkyl, aryloxy, or halogen; and
j=0, 1, or 2.

Extended chain polyethers or polyesters can be prepared, for example, by reacting the amine hub with an acid anhydride to form an acid (or acid halide) hub or with nitrophthalic anhydride to form a nitro-terminated hub.

The amine hub can be reacted with a dianhydride and an amine end cap, but these compounds are not preferred in most circumstances, since they depart from the ether/ester compounds that are the most preferred. If used, however, the dianhydride preferably is selected from the group consisting of:

(a) pyromellitic dianhydride, (b) benzophenonetetracarboxylic dianhydride (BTDA), and (c) 5-(2,5-diketotetrahydrofuryl)-3-methylcyclohexene-1,2-dicarboxylic anhydride (MCTC), but may be any aromatic or aliphatic dianhydride, such as those disclosed in U.S. Pat. Nos. 4,504,632; 4,577,034, 4,197, 397; 4,251,417; 4,251,418; or 4,251,420. Mixtures of dianhydrides might be used. Lower molecular weight dianhydrides are preferred, and MCTC or other aliphatic dianhydrides are the most preferred for lower curing multidimensional oligomers.

The dianhydride may also be a compound prepared by the condensation of an acid halide anhydride, such as phthalic acid chloride anhydride, with a diamine. In this way, extended chain ether dianhydrides can readily be prepared, and these relatively high molecular weight dianhydrides may be preferred in the extended polyether oligomers, since the imide linkages have a less significant role in the resulting oligomer structure (i.e. there is a higher density of ether linkages).

The oligomers can be formed by a homogeneous reaction scheme wherein all the reactants are mixed, or can be formed by a stepwise reaction scheme wherein the radiating chains are affixed to the hub and the product of the first reaction is subsequently reacted with the end cap groups. Of course, the hub may be reacted with chains that include one reactive functionality and a suitable terminal end cap, but creating and isolating these "chain-end group" intermediates is difficult, if not impossible. Homogeneous reaction is preferred, resulting undoubtedly in a mixture of oligomers because of the complexity of the reactions. The products of the processes (even without distillation or isolation of individual species) are preferred oligomer mixtures which can be used without further separation in advanced composites.

Oligomers can be synthesized from a mixture of four or more reactants so that extended chains may be formed, or sequential reaction is possible. For example, trihydroxybenzene may be reacted with the preferred acid chlorides, diols, (such as those used with the halide mechanism), and end cap monomers to achieve oligomers having extended chains. Adding components, however, adds to the complexity of the reaction and its control, and may result in undesirable competitive reactions or complex mixtures of macromolecules having widely different properties, because chain extenders and chain terminators are mixed, and compete against one another.

The selection of chains and end caps can effect the thermal stability, toughness, ease of processing, impact resistance, and solvent resistance of the resulting advanced composites. Longer chains will probably result in reduced thermal stability since the relative proportion (density) of crosslinking bonds will be reduced, and the crosslinking bonds will be spaced farther apart. Since the end caps exhibit different thermal properties, they will undoubtedly impart different properties to the resulting composite. End caps selected from the group consisting of:

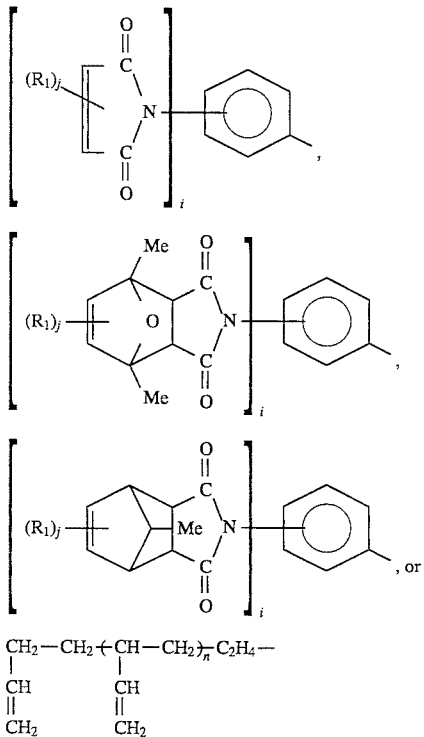

$$\begin{array}{c} CH_2-CH_2+CH-CH_2\}_n C_2H_4- \\ | \qquad\qquad | \\ CH \qquad\qquad CH \\ \| \qquad\qquad \| \\ CH_2 \qquad\qquad CH_2 \end{array}$$

will probably result in oligomers having lower thermal stability.

Although aryl backbones for the arms are preferred, aliphatic moieties may be incorporated into the arms if desired. Aliphatic moieties probably will reduce the thermal stability of the resulting composites since the bonds of aliphatic compounds are less stable than those of aromatic compounds.

Polybutadiene-capped oligomers extend the chemistry of U.S. Pat. No. 4,547,553 to multidimensional morphologies. For example, the acid halide of cyuranic acid can be reacted with hydroxy-terminated butadiene compounds to produce star oligomers. Preferably the butadiene has a predominantly atactic and vinyl composition, being more than 60% 1,2 configuration with the remainder being 1,4 configuration. Prior to reaction, the butadiene can be polymerized into relatively low molecular weight oligomers that can subsequently be reacted with the acid halide hub. These star oligomers need not be further capped, since the butadiene provides unsaturation to produce crosslinking upon curing.

Extended butadiene-capped chains can also be formed in the same manner as the linear chains of U.S. Pat. No. 4,547,553 by reacting the hub, hydroxy or carboxy terminated polybutadienes, and phenoxyphenyl compounds of the formula:

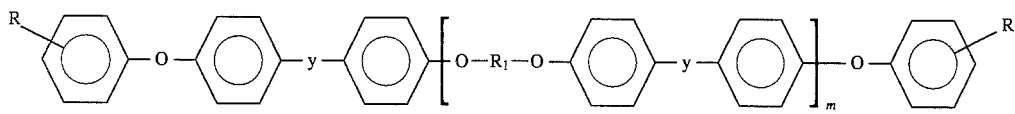

wherein
R=acid halide, carboxy, hydroxy, or lower alkyl ester;
$R_1$=diphenylisopropane, phenylene, biphenylene, diphenylenesulfide, diphenylenesulfone, diphenylene ether, or diphenylene hexafluoropropane;
m=0–4; and
y=—$SO_2$—, —S—, —SO—, —CO—, or —$(CF_3)_2C$—;
and
wherein the polybutadiene and phenoxyphenyl compounds have corresponding reactive functionalities (i.e. —OH on one and $$\begin{array}{c} O \\ \| \\ -C-X \end{array}$$

on the other) in relatively stoichiometric proportion.

Short chains having formula weights below about 1500 per arm, and, preferably, about 500 per arm, are preferred.

Oligomers of the present invention may be used to form prepregs by the conventional method of impregnating a suitable fabric with a mixture of the oligomers and a solvent. Suitable coreactants may be added to the solvent, if desired, when preparing prepregs.

The prepregs may be cured by conventional vacuum bag techniques to crosslink the end caps. Temperatures suitable for curing are in the range of 150°–650° F. The resulting product is a cured, thermally stable, solvent-resistant composite. The crosslinked oligomer may also be used as an adhesive, and curing such adhesives may be filled, if desired.

If the oligomers include Schiff base or other "conductive" linkages, the resulting oligomers might be conductive or semiconductive, if suitably doped. Dopants for creating semiconductive or conductive composites are preferably selected from compounds commonly used to dope other polymers, namely (1) dispersions of alkali metals (for high activity) or (2) strong chemical oxidizers, particularly alkali perchlorates (for lower activity). Arsenic compounds and elemental halogens, while active dopants, are too dangerous for general usage, and are not recommended.

The dopants react with the polymers to form charge transfer complexes. N-type semiconductors result from doping with alkali metal dispersions. P-type semiconductive result from doping with elemental iodine or perchlorates.

While research into conductive or semiconductive polymers has been intense, the resulting compounds (mainly polyacetylenes, polyphenelenes, and polyvinylacetylenes) are unsatisfactory for aerospace applications because the polymers are:

(a) unstable in air;

(b) unstable at high temperatures;

(c) brittle after doping;

(d) toxic because of the dopants; or (e) intractable.

These problems may be overcome or significantly reduced with the conductive oligomers of the present invention.

While conventional theory holds that semiconductive polymers should have (1) low ionization potentials, (2) long conjugation lengths, and (3) planar backbones, there is an inherent trade-off between conductivity and toughness or ease of processing, if these constraints are followed. To overcome the processing and toughness shortcomings common with Schiff base, oxazole, imidazole, or thiazole oligomers, the oligomers of the present invention, include "sulfone" linkages interspersed along the backbone providing a mechanical swivel for the rigid, conductive segments of the arms.

Since it is difficult to include the oxazole, imidazole, or thiazole linkages in the reactants, Schiff base compounds are preferred. The principle focus of the invention is toward multidimensional ethers and esters, and the conductive or semiconductive composites are not the preferred compounds of the present invention. They are but a small subset of the compounds that comprise the present invention.

Solubility of the oligomers becomes an increasing problem as the length of the backbones (arms) increases. Therefore, shorter backbones are preferred, so long as the resulting oligomers remain processible. That is, the backbones should be long enough to keep the oligomers soluble the reaction sequence.

Blends of the crosslinkable oligomers and noncrosslinking, compatible polymers can also be made. These blends generally comprise substantially equimolar mixtures of the oligomer and polymer, although other ratios can be used. The polymer usually has a backbone substantially identical with the oligomer.

Composites made from the blends can have improved impact resistance while retaining the desired solvent resistance. Generally, the blend includes capped oligomers to provide crosslinking upon curing and noncrosslinking polymers of a corresponding backbone to provide compatibility of the oligomer and polymer. A 50—50 blend on a molar basis of oligomers and polymer may be formed by (a) dissolving the capped oligomer in a suitable first solvent, (b) dissolving the uncapped polymer in a separate portion of the same solvent or in a solvent miscible with the first solvent, (c) mixing the two solvent solutions to form a lacquer, and (d) applying the lacquer to fabric in a conventional prepregging process.

Although the polymer in the blend usually has the same backbone (structure and formula weight) as the oligomer, the properties of the composite formed from the blend can be adjusted by altering the ratio of formula weight for the polymer and oligomer.

The terminal groups of the polymer are unimportant so long as the polymer's terminal groups do not react with or impede the crosslinking of the oligomer end caps. Also, it is probably nonessential that the oligomer and polymer have identical repeating units (structure), but that the oligomer and polymer merely be compatible in the solution prior to sweeping out as a prepreg. Of course, if the polymer and oligomer have identical backbones, compatibility in the blend is more likely.

The noncrosslinking polymer can be made by the same synthetic method as the oligomer with the substitution of a quenching cap for the crosslinking end cap. For example, phenol can replace end caps of the formula A-OH; aniline can replace end caps of the formula A-NH$_2$; and, nitrobenzene can replace end caps of the formula A-NO$_2$.

While the best blends are probably those in which the backbones are essentially identical and of modest formula weight and those in which the oligomer and polymer are in equimolar proportions, other variant blends may be prepared, as will be recognized by those of ordinary skill in the art.

Solvent resistance may decrease markedly if the comparable polymer is provided in large excess to the crosslinkable oligomer in the blend.

As discussed, the blends will generally comprise a mixture of one oligomer and a polymer of the same type. The polymer may, however, be from another chemical family, such as imide or amide. The mixture may include multiple oligomers or multiple polymers, such as a three component mixture of ether and ester oligomers and an ether polymer. Other combinations will be recognized by those of ordinary skill in the art.

The blends may yield semi-interpenetrating networks of the general type described by Egli et al., "Semi-Interpenetrating Networks of LARC-TPI" available from NASA-Langley Research Center.

The oligomers can be combined with reinforcing materials in fiber, chopped fiber, whisker, or fabric form, and may be ceramic, organic, carbon (graphite), or glass, as suited for the desired application.

The following examples illustrate features of the present invention:

EXAMPLE I

An ester star oligomer was prepared by dissolving 162.14g phloroglucinol dihydrate in a solution of about 36.04g H$_2$O and 127.4g of solvent containing 27% xylene and 73% DMAC. In a Barrett trap under a bubbling N$_2$ atmosphere, the mixture was refluxed to strip off the H$_2$O and, then, the xylene. After the stripping step, the resulting DMAC solution was slowly cooled to about 0° C. before adding 333.93g of triethylamine (TEA) (30% excess) while the solution was stirred. After 10 min. of stirring, 905.19g of p-nadicimidobenzoylchloride were added, and the product was rinsed with DMAC. Stirring continued thereafter for 2 hours, before a product was recovered by adding a suitable amount of HCl. The product was a white solid powder at room temperature having the following characteristics:

| | |
|---|---|
| molten, bubbly amber | 160–225° C.; |
| brittle crystals | 225–250° C.; |
| clear amber liquid | 250–300° C.. |

Above 300° C., the product began to gel, finally forming a crystalline powder.

EXAMPLE II

Another ester star oligomer was prepared by dissolving 162.14g phloroglucinol dihydrate in a xylene/DMAC mixture having about 740g xylene and 2000g DMAC. Refluxing the mixture in a Barrett trap under a N$_2$ atmosphere stripped H$_2$O, which was generated by the reaction. Upon heating to about 160° C., the xylene was also stripped from the mixture. After cooling the DMAC solution to ambient, about 3.0 moles 4-hydroxyphenylnadimide and about 6.1 moles TEA were added. The resulting mixture was stirred in an ice bath while 1582.11g of the acid chloride of bis-(4,4'-carboxyphenoxyphenylsulfone) was slowly added. After the addition, the stirring was continued for 2 hr. The product was soluble in the reaction mixture, but coagulated in H$_2$O to a white powder which softened at about 165° C. The powder was washed with deionized water to remove residual chloride. The powder was insoluble in acetone or methyl ethyl ketone, formed a slightly milky solution upon dissolution in tetrahydrofuran, and was soluble in methylene chloride.

EXAMPLE III

An ether star oligomer was prepared by charging 522g DMAC, 193g xylene, 1.2 moles K$_2$CO$_3$, and 3.0 moles 4-hydroxyphenylnadimide to a reaction flask fitted with a stirrer, condenser, thermometer, and $N_2$ purge. About 1.0 moles phloroglucinol dihydrate was added, and the mixture was refluxed until all $H_2O$ in the flask was expelled and no additional $H_2O$ was generated. After cooling the resulting intermediate mixture, about 3.0 moles of 4,4'-dichlorodiphenylsulfone was added, and the flask was reheated to about 150° C. to strip the xylene from the solution. Refluxing continued for 16 hours at about 150° C. Upon removal of all the xylene, the flask was heated to about 160°–164° C. for 2 more hours. After cooling, the product was recovered by adding $H_2O$ to induce coagulation while mixing the solution in a Waring blender. The coagulate was thoroughly washed with deionized $H_2O$ until the residual chloride ion was removed. The product was a dark brown, fine grain powder which softened at about 150° C. and rehardened slightly at about 260° C.

EXAMPLE IV

An ether star oligomer or prepolymer was made by charging 3.78 kg DMSO, 1.62 kg toluene, 6.0 moles NaOH, 1.0 mole-phloroglucinol dihydrate, and 3.0 moles p-aminophenol to a reaction flask fitted with a stirrer, condenser, thermometer and a $N_2$ purge. The solution was refluxed until no additional water was generated or stripped in the condenser and, the, the temperature was increased to about 160° C. to strip the toluene. After the toluene was removed, the flask was allowed to cool to ambient temperature before 3.0 moles of 4,4'-dichlorodiphenylsulfone were added. The resulting mixture was reheated to about 160° C. and held there for 4–8 hours. Upon cooling to ambient temperature, the product was obtained by inducing coagulation by adding an aqueous solution of about 2 wt. % NaOH and 1 wt. % $Na_2SO_3$, while mixing in a Waring blender. The coagulate was washed with deionized $H_2O$ to remove residual chloride ions. The product melted at about 110°–125° C.

About 1096.21g of the product were, then, charged to another flask with 4.28 kg DMAC and 2.13 kg toluene. Refluxed under a $N_2$ atmosphere until all water that was generated was removed the solution was then heated to strip the toluene from it. After cooling, 3.09 moles of nadic anhydride was added slowly, taking care to prevent any exothermic reaction. The mixture was stirred in an ice bath for about 2 hours. The resulting oligomer product was then recovered by conventional steps.

EXAMPLE V

The method of Example IV was followed except that the second flask was charged with dry DMAC/toluene, the intermediate product, and the nadic anhydride. Then, the solution was refluxed to remove all $H_2O$ that was generated, and the product oligomer was recovered by coagulating the oligomer in a Waring blender by adding water to the cooled reaction mixture.

EXAMPLE VI

An ester star-burst oligomer was prepared according to the method of Example II, except that about 3.0 moles of hydroxy-2,4-phenyldinadimide was added instead of the 4-hydroxyphenylnadimide. The resulting oligomer included difunctional crosslinkable end caps.

EXAMPLE VII

The ether star oligomer of Example III and a graphite fiber were combined to form a graphite-resin composite, which was tested using thermographimetric analysis (TMA) to determine the glass transition temperature of the resinous composite. A minimum corresponding to the glass transition temperature occurred at about 523.9° C.

EXAMPLE VIII

Mechanical properties were determined for three, speciments of 10-ply graphite-oligomer composites made with the ester star oligomer of Example II. The data obtained for interlaminar shear at ambient temperature was:

|  | Specimen No. | | |
| --- | --- | --- | --- |
|  | 1 | 2 | 3 |
| Thickness (in) | 0.0631 | 0.0616 | 0.0633 |
| Width (in) | 0.2492 | 0.2515 | 0.2478 |
| Ultimate Load (lbs) | 93 | 101 | 90 |
| Ultimate Stress (psi) | 4,436 | 4,890 | 4,303 |

EXAMPLE IX

Mechanical properties were determined for four specimens of graphite oligomer composites made with the ester star-burst oligomer of Example VI. The data obtained for interlaminar shear at ambient temperature was:

|  | Specimen No. | | | |
| --- | --- | --- | --- | --- |
|  | 1 | 2 | 3 | 4 |
| Thickness (in) | 0.0814 | 0.0834 | 0.0824 | 0.0823 |
| Width (in) | 0.2500 | 0.2491 | 0.2497 | 0.2488 |
| Ultimate Load (lbs) | 270 | 290 | 270 | 267 |
| Ultimate Stress (psi) | 9,951 | 10,469 | 9,842 | 9.780 |

A second set of three speciments were also tested to confirm the mechanical properties. The data was:

|  | Specimen No. | | |
| --- | --- | --- | --- |
|  | 1 | 2 | 3 |
| Thickness (in) | 0.0808 | 0.0826 | 0.0830 |
| Width (in) | 0.2470 | 0.2495 | 0.2460 |
| Ultimate Load (lbs) | 300 | 323 | 325 |
| Ultimate Stress (psi) | 11,274 | 11,755 | 11,938 |

EXAMPLE X (Hypothetical)

One mole of cyuranic acid chloride can be reacted with three moles of

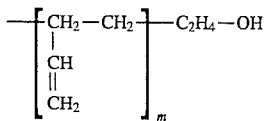

in a suitable solvent under an inert gas atmosphere to yield a polybutadiene oligomer exhibiting multidimensional morphology.

While para isomerization is shown, other isomers are possible. Furthermore, the aryl groups can have substituents, if desired, such as halogen, lower alkyl up to about 4 carbon atoms, lower alkoxy up to about 4 carbon atoms, or aryl. Substituents may create steric hindrance problems in synthesizing the oligomers or in crosslinking the oligomers into the final composites.

While preferred embodiments have been described and several detailed examples have been presented, those skilled in the art will readily recognized alterations, modifications, or variations that might be made without departing from the inventive concept. The examples serve only to illustrate particular features of the invention and are not meant to limit it. Accordingly, the invention should be construed broadly in light of this disclosure, and should only be limited as is necessary in view of the pertinent prior art.

We claim:

1. An extended multidimensional ether oligomer obtainable by the process comprising the step of condensing a mixture of Ar—(—Q)$_w$, M—R—M, and Y$_i$—φ—Q wherein Ar=an aromatic radical of valency w, w=a small integer greater than or equal to 3, Q=—OH, —X, or —NO$_2$;

M=—X or —NO$_2$, if Q=—OH, and —OH, if Q=—X or —NO$_2$

φ=phenylene, i=1 or 2,

Y=

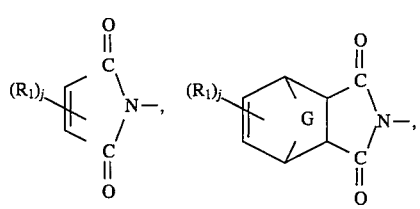

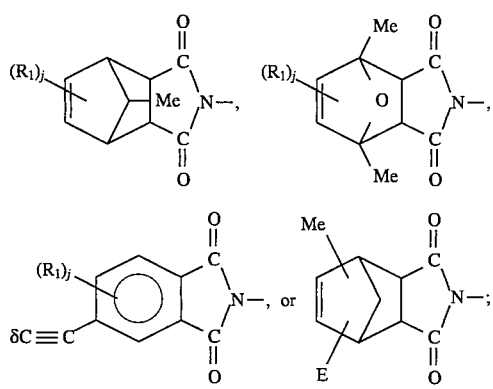

X=halogen;

j=0, 1, or 2;

Me=methyl;

E=allyl or methallyl;

G=—CH$_2$—, —O—, —S—, —SO$_2$—, —SO—, —CO—, —CHR$^1$—, or —C(R$^1$)$_2$—;

R$_1$=lower alkyl, lower alkoxy, aryl, aryloxy, substituted alkyl, substituted aryl, or mixtures thereof;

R=a hydrocarbon radical; and

δ and R$^1$=any of hydrogen, lower alkyl, or phenyl.

2. An extended polyester, multidimensional oligomer obtainable by the process comprising the steps of condensing a mixture of Ar—(—Q)$_w$, M—R—M, and Y$_i$—φ—Q wherein Ar=an aromatic radical of valency w;

w=an integer greater than or equal to 3;

Q=—OH or —COX;

M=—COX, if Q=—OH, and —OH, if Q=—COX;

X=halogen;

i=1 or 2;

φ=phenylene;

R=a hydrocarbon radical;

Y=

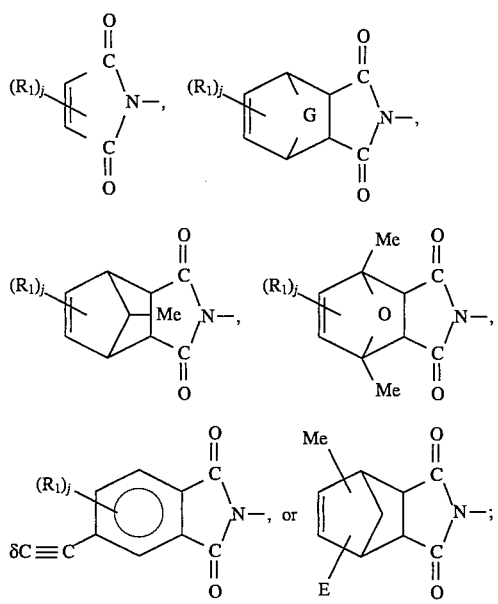

E=allyl or methallyl;

X=halogen;

j=0, 1, or 2;

Me=methyl;

G=—CH$_2$—, —O—, —SO$_2$—, —S—, —SO—, —CO—, —CHR$^1$—, or —C(R$^1$)$_2$—; and

R$_1$=lower alkyl lower alkoxy, aryl, aryloxy, substituted alkyl, substituted aryl, halogen or mixtures thereof; and δ and R$^1$=any of hydrogen, lower alkyl, or phenyl.

3. The oligomer of claim 1 further comprising a reinforcing additive in fiber of particulate form.

4. The oligomer of claim 1 further comprising a reinforcing additive in fiber of particulate form.

5. A composite formed by curing the oligomer of claim 1.

6. A composite formed by curing the oligomer of claim 1.

7. A composite formed by curing the oligomer of claim 2.

8. A composite formed by curing the oligomer of claim 3.

9. The oligomer of claim 1 wherein Ar is phenylene.

10. The oligomer of claim 1 wherein Ar is phenylene.

11. The oligomer of claim 1 wherein i is 2.

12. The oligomer of claim 1 wherein i is 2.

13. The oligomer of claim 1 wherein R is selected from the group consisting of:

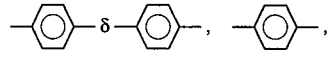

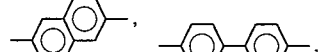

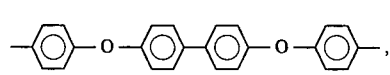

-continued

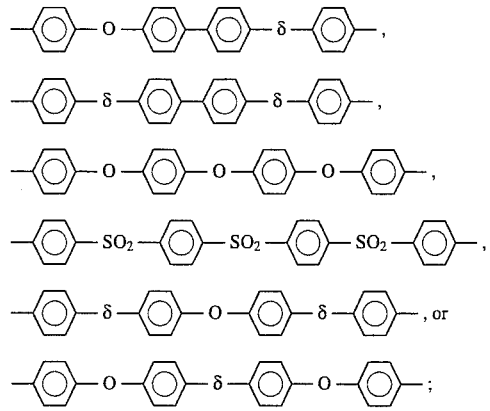

wherein q=—CO—, —SO₂—, —(CF₃)₂C—, or —S—.

14. The oligomer of claim 1 wherein R is selected from the group consisting of:

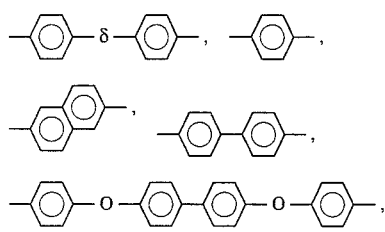

-continued

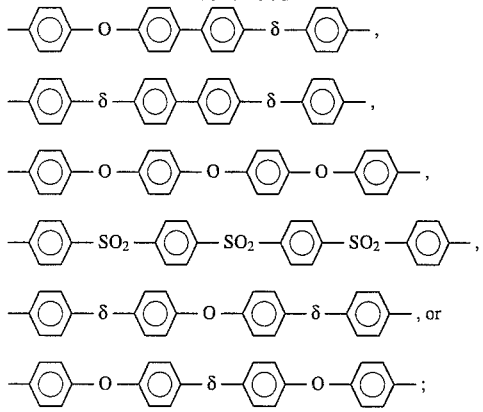

wherein q=—CO—, —SO₂—, —(CF₃)₂C—, or —S—.

15. The oligomer of claim 1 wherein occurs sequentially with the condensation of Ar—(—Q)$_w$ with M—R—M to form an intermediate with subsequent condensation of the intermediate with Y$_i$—φ—Q.

16. The oligomer of claim 1 wherein occurs sequentially with the condensation of Ar—(—Q)$_w$ with M—R—M to form an intermediate with subsequent condensation of the intermediate with Y$_i$—φ—Q.

* * * * *